(12) United States Patent
Cheon et al.

(10) Patent No.: US 8,722,674 B2
(45) Date of Patent: May 13, 2014

(54) 1,3,5-TRIAZINE-2,4,6-TRIAMINE COMPOUND OR PHARMACEUTICAL ACCEPTABLE SALT THEREOF, AND PHARMACEUTICAL COMPOSITION COMPRISING THE SAME

(75) Inventors: Hyae Gyeong Cheon, Daejeon (KR); Kwang-Rok Kim, Daejeon (KR); Sang Dal Rhee, Daejeon (KR); Won Hoon Jung, Daejeon (KR); Jong-Cheol Lee, Daejeon (KR); Sung Wuk Kim, Seongnam-si (KR); Sung Soo Jun, Seongnam-si (KR)

(73) Assignee: Hanall Biopharma Co., Ltd., Daejeon (KR)

( * ) Notice: Subject to any disclaimer, the term of this patent is extended or adjusted under 35 U.S.C. 154(b) by 372 days.

(21) Appl. No.: 12/674,886

(22) PCT Filed: Aug. 28, 2008

(86) PCT No.: PCT/KR2008/005062
§ 371 (c)(1),
(2), (4) Date: Feb. 23, 2010

(87) PCT Pub. No.: WO2009/028891
PCT Pub. Date: Mar. 5, 2009

(65) Prior Publication Data
US 2011/0237587 A1    Sep. 29, 2011

(30) Foreign Application Priority Data
Aug. 31, 2007    (KR) .................. 10-2007-0088115

(51) Int. Cl.
*A61K 31/53* (2006.01)
*C07D 251/54* (2006.01)
*C07D 403/00* (2006.01)
*C07D 251/70* (2006.01)

(52) U.S. Cl.
CPC ............... *C07D 251/70* (2013.01); *A61K 31/53* (2013.01)
USPC ............ 514/245; 544/196; 544/198; 544/200

(58) Field of Classification Search
USPC .......................................... 544/196, 200, 198
See application file for complete search history.

(56) References Cited

U.S. PATENT DOCUMENTS

| 3,759,911 | A | * | 9/1973 | Irikura et al. ................. 544/198 |
| 3,919,221 | A |   | 11/1975 | Dazzi |
| 4,136,092 | A | * | 1/1979 | Jackle et al. .................... 528/60 |
| 5,272,192 | A | * | 12/1993 | Wehner et al. ................. 524/87 |

FOREIGN PATENT DOCUMENTS

| JP | 01226879 | 9/1989 |
| JP | 2006-016506 | 1/2006 |
| WO | WO 93/18793 | 9/1993 |
| WO | WO 97/00277 | 1/1997 |
| WO | WO 2004/003198 | 1/2004 |
| WO | WO 2007/079916 | 7/2007 |

OTHER PUBLICATIONS

Bielejewska et al. (2001) Journal of the American Chemical Society 123(31):7518-7533 "Thermodynamic Stabilities of Linear and Crinkled Tapes and Cyclic Rosettes in Melamine—Cyanurate Assemblies: A Model Description".
Borkovec and DeMilo (1967) Journal of Medicinal Chemistry 10(3):457-461 "Insect Chemosterilants. V. Derivatives of Melamine".
Qin et al. (2005) Analytical Chemistry 77(16):5302-5310 "Chiral Melamine Derivatives: Design, Synthesis, and Application to Mass Spectrometry-Based Chiral Analysis".
Walker et al. (1950) Journal of the American Pharmaceutical Association 39:393-396 "Arylaminoheterocycles V Anilino-*s*-triazines".

* cited by examiner

*Primary Examiner* — Shengjun Wang
(74) *Attorney, Agent, or Firm* — Swanson & Bratschun, LLC

(57) ABSTRACT

Disclosed herein are a 1,3,5-triazine-2,4,6-triamine compound or a pharmaceutically acceptable salt thereof, a preparation method thereof, and a composition for preventing or treating metabolic syndromes, diabetes, or cancers with deletion of P53 gene, which comprises the same.

5 Claims, No Drawings

# 1,3,5-TRIAZINE-2,4,6-TRIAMINE COMPOUND OR PHARMACEUTICAL ACCEPTABLE SALT THEREOF, AND PHARMACEUTICAL COMPOSITION COMPRISING THE SAME

RELATED APPLICATIONS

This application is a 35 U.S.C. §371 national phase application of PCT/KR2008/005062 (WO 2009/028891), filed on Aug. 28, 2008, entitled "1,3,5-Triazine-2,4,6-Triamine Compound or Pharmaceutical Acceptable Salt Thereof, and Pharmaceutical Composition Comprising the Same", which application claims the benefit of Korean Application Serial No. 10-2007-0088115, filed Aug. 31, 2007, which is incorporated herein by reference in its entirety.

TECHNICAL FIELD

The present invention relates to a substance for preventing or treating metabolic syndromes, diabetes, or cancers with deletion of P53 gene, and more particularly to a 1,3,5-triazine-2,4,6-triamine compound or a pharmaceutically acceptable salt thereof, a preparation method thereof, and a composition for preventing or treating metabolic syndromes, diabetes, or cancers with deletion of P53 gene, which contains the same.

BACKGROUND ART

Diabetes is a disease characterized by continued high blood glucose levels. The major conditions of diabetes are carbohydrate metabolism abnormality and lipid metabolism abnormality, and systemic complications of diabetes grow worse due to blood flow disturbance caused by high blood glucose levels and due to a decrease in sugar utilization. Such diabetic conditions are caused by the deficiency of hormone insulin, which regulates carbohydrate and lipid metabolisms, or insulin resistance.

Diabetes caused by the inability to secrete insulin is called "type 1 diabetes", and diabetes caused by insulin resistance is called "type 2 diabetes".

About 10% of the population in Korea was reported to be diabetic patients, and more than 90% of these patients are type 2 diabetic patients. In USA, there are nearly 20,000,000 diabetic patients, and about 95% of these diabetic patients are type 2 diabetic patients and are mainly obese people more than 45 years old. The incidence of type 2 diabetes is rapidly increasing worldwide, and the age of people suffering from type 2 diabetes also becomes young. Furthermore, Korea has the highest number of deaths caused by diabetes among OECD countries (March, 2007, Korean Medical Association).

Insulin is a hormone secreted by the β cells of the Langerhans islets in the pancreas. It regulates glucose metabolism and promotes the transport of glucose from the blood to the skeletal muscle, liver, adipose tissue, and other tissues, such that it can be utilized as an energy source or biosynthesized and stored as glycogen or fat.

Type 2 diabetes is a condition in which the body becomes resistant to insulin secreted from the pancreas, and the major function of insulin is impaired. It is a disease in which blood vessels are directly destroyed due to hyperinsulinemia, and metabolic syndrome becomes more severe. The mortality caused by diabetic complications is rapidly increasing worldwide.

Insulin resistance is a state in which insulin does not exhibit a function of transporting glucose into cells, due to the decrease of insulin receptor or due to the deficiency of receptor or signal transduction pathways through receptor. Such insulin resistance also appears obese persons or glucose-intolerant persons, who become diabetic. Such persons show an increase in blood glucose levels, even though insulin is normally secreted from the pancreas, and they become diabetic after several years, if the insulin resistance is not treated. The first stage of development of type 2 diabetes starts from insulin resistance in adipose tissue. In this stage, diabetes does not yet occur, but lipid metabolism abnormality appears due to insulin resistance. This stage is the disease condition of pre-diabetic obese persons or glucose-intolerant persons, the blood glucose levels of which increase to normal levels or higher, if they take glucose. Thus, though they are not diabetic, they can be prevented from the development of diabetes by treating insulin resistance. The present invention aims to invent a compound which can be used not only for the treatment of diabetes, but also for the prevention of development of diabetes.

The next stage is the stage of insulin resistance in not only adipose tissue, but also liver tissue or muscular tissue, which is the disease condition of type 2 diabetic patients. The compound of the present invention is a material that solves insulin resistance in adipose tissue, liver tissue and muscular tissue.

Many kinds of anti-diabetic drugs have been used to treat type 2 diabetes. However, drugs excluding biguanide metformin are primarily successful in lowering blood glucose levels, but do not show satisfactory effects on the prevention of important complications, including visual loss, heart failure, stroke, renal failure, peripheral neuropathy, foot ulcer, etc. Thus, through a guide for the use of anti-diabetic drugs (published in Diabete Care, August, 2006), the American Diabetes Association and the European Association for the Study of Diabetes commonly recommended to necessarily start treatment with metformin in type 2 diabetes. Also, the Korean Diabetes Association already started to recommend metformin as a primary drug (a report by the Research Institute for Healthcare Policy of Korean Medical Association, March, 2007).

Metformin is the only drug that has the same effect as that of insulin. However, it is an oral drug that does not cause a low blood glucose problem occurring in the case of insulin. Metformin is a drug that solves a problem of insulin resistance in adipose tissue, liver tissue and muscular cells. In addition, the blood glucose-lowering action and glycosylated hemoglobin level lowering action thereof are the most potent among all oral anti-diabetic drugs, and it has little or no side effects.

Sulfonylurea-based drugs, which have frequently been used to date, are drugs that lower blood glucose levels by enforcing insulin to be secreted from the pancreas. They accelerate the secretion of insulin in type 2 diabetic patients in which insulin secretion already decreased, and thus the degradation of secretory function of the pancreas is accelerated, such that the drug effect disappears and insulin injection is required. In addition, they can make lipid metabolism abnormal by promoting arteriosclerosis, increasing bodyweight and inducing low blood glucose levels, thus causing brain injuries.

Moreover, glitazone drugs appeared as drugs that solve the insulin resistance problem, but have no sufficient effect on blood glucose lowering, because they solve insulin resistance mainly in adipose tissue. For this reason, in most cases, they must be used in combination with metformin. A more important problem is that close attention is required in the use thereof, because mechanisms of side effects such as retinal vascular occlusion have been clearly found. Other oral anti-diabetic drugs are blood glucose lowering agents which are limited only to blood glucose lowering after a meal.

It can be seen in several papers that only metformin among oral anti-diabetic drugs is a drug of primary choice. Particularly, it was demonstrated that the effect of metformin activates AMPK, and thus the propriety of clinical effects thereof was demonstrated. AMPK is a key enzyme that physiologically regulates carbohydrate metabolism and lipid metabolism, and it was reported that metformin activates the enzyme, and thus has the effects of normalizing blood glucose levels, improving lipid conditions, normalizing irregular menstruation, ovulation and pregnancy, treating fatty liver, and preventing and treating cancers with deletion of P53 gene.

According to a report (Cancer research, July, 2007) by the Abramson Cancer Center of the University of Pennsylvania, metformin, an AMPK activator, is effective for the prevention and treatment of cancers with deletion of P53 gene. Accordingly, a compound of formula 1 according to the present invention, which has AMPK activity, can be effective for the prevention and treatment of cancer with deletion of P53 gene.

Metformin is administered three times a day, and the dosage thereof is more than 500 mg. Thus, to make sustained-release tablets which are administered once a day, tablets containing 1500-2250 mg of metformin must be prepared. These tablets are difficult to take, because they have a very large size. Accordingly, current sustained-release tablets, which are administered once at 24-hr intervals, are sold, containing only 750 mg of metformin per tablet.

DISCLOSURE OF INVENTION

Technical Problem

Therefore, it is an object of the present invention to invent a novel substance, which shows blood glucose-lowering and lipid-lowering effects, the main effects of AMPK, and has improved advantages over metformin, while maintaining a biguanide structure that is the skeletal molecular structure of metformin.

Moreover, the present invention aims to develop a drug, which exhibits blood glucose-lowering and lipid-lowering effects and has a reduced dosage while maintaining a biguanide structure that is the skeletal molecular structure of metformin. In the case of sustained-release preparations which are currently commercially available, more than two tablets must be administered, because they contain 750 mg of metformin. However, if the compound according to the present invention is used, there are advantages in that the daily required dosage is reduced due to the excellent effect thereof, and thus the number of tablets to be administered can be reduced.

Technical Solution

The present invention provides a 1,3,5-triazine-2,4,6-triamine compound of Formula 1 or a pharmaceutically acceptable salt thereof, a preparation method thereof and a pharmaceutical composition the same:

[Formula 1]

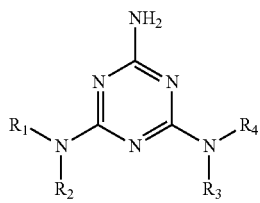

1 wherein $R_1$ and $R_2$ each independently represents hydrogen or a (C1-C5)alkyl; and $R_3$ and $R_4$ each independently represents hydrogen, a (C1-C7)alkyl, a (C3-C7)cycloalkyl, a phenyl group, a phenyl(C1-C3)alkyl group, a naphthyl group, a napthyl (C1-C3)alkyl group, a (C3-C7)heterocycloalkyl(C1-C6)alkyl, a heteroaryl or heteroaryl(C1-C6)alkyl, or $R_3$ and $R_4$, together with nitrogen to which they are attached, form a (C3-C8)heterocycloalkyl, wherein the phenyl or naphthalene may be substituted with a substituent selected from the group consisting of a halogen atom, a hydroxyl group, a nitro group, a cyano group, a (C1-C6)alkyl group, a (C1-C6)haloalkyl group, a (C3-C6)cycloalkyl group, a (C6-C10)aryl group, a (C6-C10)aryloxy group, a (C1-C6)alkoxy group, a (C1-C6)haloalkoxy group, a (C3-C6)cycloalkyloxy group, a (C1-C7)alkanoyl group, a carboxyl group, a carbamoyl group, an alkylamino group, a (C2-C7)sulfonic acid group, a sulfonamido group, and a (C1-C6)alkylthio group.

Preferably, the compound of Formula 1 is a 1,3,5-triazine-2,4,6-triamine compound wherein $R_3$ and $R_4$ in Formula 1 are each independently hydrogen, methyl, ethyl, n-propyl, isopropyl, n-butyl, isobutyl, sec-butyl, tert-butyl, n-hexyl, n-heptyl, cyclopropyl, cyclobutyl, cyclopentyl, cyclohexyl, cycloheptyl, benzyl, 1-phenylethyl, 2-phenylethyl, 1-phenylpropyl, 2-phenylpropyl, 3-phenylpropyl, 1-napthylmethyl, 2-napthylmethyl, 1-napthylethyl, 2-napthylethyl, 1-piperidylmethyl, 1-piperidylethyl, 4-piperidylmethyl, 4-piperidylethyl, 1-morpholinylmethyl, 1-morpholinylethyl, 1-pyrrolidin-2-one-propyl, 2-pyridylmethyl, 3-pyridylmethyl, 4-pyridylmethyl, 2-furylmethyl, 2-furylethyl, 2-thiazolylmethyl or 2-thiazolylethyl; wherein said phenyl group or naphthalene may be substituted with a substituent selected from the group consisting of a halogen atom, a hydroxyl group, a nitro group, a cyano group, a (C1-C6)alkyl group, a (C1-C6)haloalkyl group, a (C3-C6)cycloalkyl group, a (C6-C10)aryl group, a (C6-C10)aryloxy group, a (C1-C6)alkoxy group, a (C1-C6)haloalkoxy group, a (C3-C6)cycloalkyloxy group, a (C1-C7)alkanoyl group, a carboxyl group, a carbamoyl group, an alkylamino group, a (C2-C7)sulfonic acid group, a sulfonamido group and a (C1-C6)alkylthio group.

Advantageous Effects

According to the present invention, there is provided a pharmaceutical composition for preventing or treating metabolic syndromes, diabetes, or cancers with deletion of P53 gene, which contains, as an active ingredient, a 1,3,5-triazine-2,4,6-triamine compound, represented by Formula 1, or a pharmaceutically acceptable salt thereof.

BEST MODE

Pharmaceutically acceptable salts of the compound of Formula 1 according to the present invention include salts with organic acids, for example, formic acid, acetic acid, propionic acid, lactic acid, butyric acid, isobutyric acid, trifluoroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranilic acid, benzenesulfonic acid, p-toluenesulfonic acid and methansulfonic acid, and salts with inorganic acids, for example, hydrochloric acid, bromic acid, sulfuric acid, phosphoric acid, nitric acid and boric acid. The above-mentioned acid addition salts are prepared by a general salt preparation method comprising: a) mixing the compound of Formula 1 directly with acid; b) dissolving one of them in a solvent or a water-containing solvent and mixing the solution with the other one; or c) placing the compound of Formula 1 in either a solvent or an acid in a water-containing solvent and mixing them.

If the compound of Formula 1 has an acidic group, for example, a carboxyl group and a sulfonic acid group, the compound of Formula 1 becomes an amphoteric salt. Examples of such a salt may include alkali metal salts, for example, sodium salt and potassium salt, alkaline earth metal salts, for example, calcium salt and magnesium salt, salts with inorganic acid, for example, aluminum salt and ammonium salt, and basic addition salts, for example, salts with organic acids, for example trimethylamine, triethylamine, pyridine, picoline, ethanolamine, diethanolamine, triethanolamine, dicyclohexylamine and N,N'-dibenzylethylenediamine. Also, salts of the compound of Formula 1 may be salts with basic amino acids, for example, arginine, lysine and ornithine, or acidic amino acids, for example, aspartic acid. The salt of the compound of Formula 1 is preferably a pharmaceutically acceptable salt, more preferably an acid addition salt, and even more preferably acetate, hydrochloride, hydrobromide, methane sulfonate, malonate or oxalate.

The compound of Formula 1 of the present invention or a salt thereof, which are used as an active ingredient, can be prepared in the following manner.

A method of preparing the compound of Formula 1 (preparation method 1) is shown in Reaction Scheme 1 wherein $NR_3R_4$ is a phenylalkyl group. First, dimethyl cyanocarbonodithioimidate (a compound of Formula 2) and a $NR_3R_4$ derivative are allowed to react in a solvent, for example, methanol, ethanol, propanol, isopropanol, butanol, benzene, toluene, xylene, ethyl acetate, tetrahydrofuran, acetonitrile or N,N-dimethylformamide, to prepare a cyanocarbaimidothioate derivative (a compound of Formula 3). The amount of $NR_3R_4$ used is about 1-2 molar equivalents based on the compound of Formula 2, and the reaction temperature generally ranges from room temperature to the reflux temperature of the solvent.

[Reaction Scheme 1]

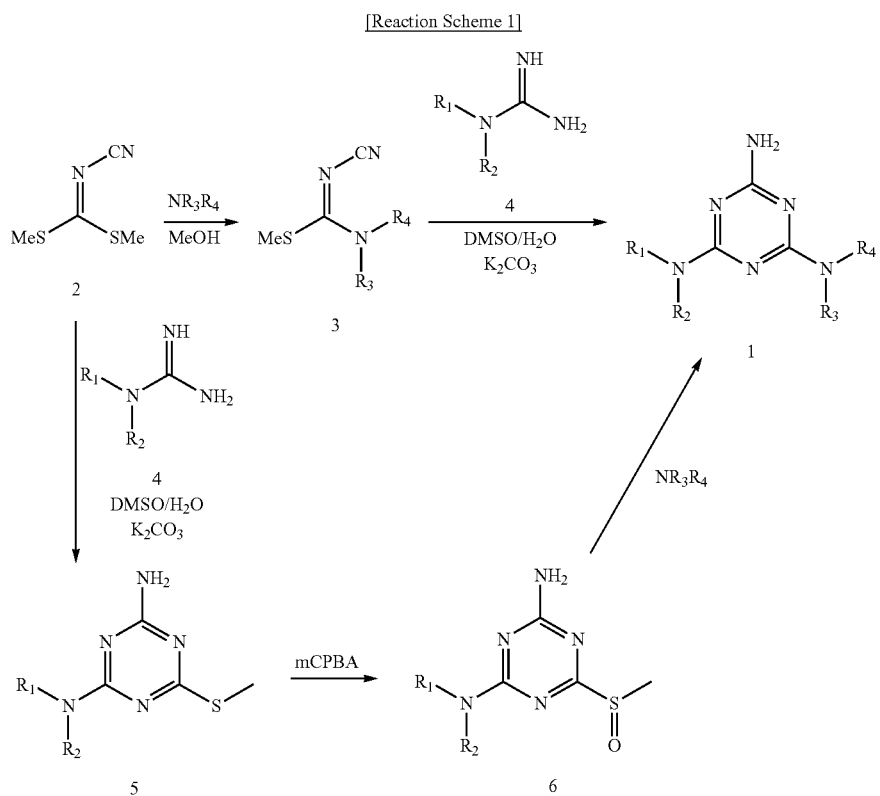

Then, the compound of Formula 3 is allowed to react with a guanidine derivative (a compound of Formula 4) in a solvent (for example, methanol, ethanol, propanol, isopropanol, butanol, benzene, toluene, xylene, ethyl acetate, tetrahydrofuran, acetonitrile, N,N-dimethylformamide, dimethylsulfoxide, water, or a mixed solvent of two or more thereof) in the presence of a base to prepare the desired compound of Formula 1. The base (e.g., piperidine, pyridine, triethylamine, sodium hydroxide, potassium hydroxide, potassium carbonate, etc.) and the guanidine derivative are used in an amount of about 1-2 molar equivalents per mole of the compound of Formula 3, and the reaction temperature ranges from room temperature to the reflux temperature of the solvent.

In the present invention, compounds represented by Formula 1, excluding a compound in which $NR_3R_4$ is a phenylalkyl group, are prepared through preparation methods of obtaining compounds 5 and 6 using dimethyl cyanocarbonodithioimidate (the compound of Formula 2) as a starting material, among the methods shown in Reaction Scheme 1. Specifically, dimethyl cyanocarbonodithioimidate (the compound of Formula 2) is allowed to react with a guanidine derivative (the compound of Formula 4) in a solvent (for example, methanol, ethanol, propanol, isopropanol, butanol, benzene, toluene, xylene, ethyl acetate, tetrahydrofuran, acetonitrile, N,N-dimethylformamide, dimethylsulfoxide, water, and a mixed solvent of two or more thereof) in the presence of a base to prepare a compound of Formula 5. The base (for example, piperidine, pyridine, triethylamine, sodium hydroxide, potassium hydroxide, potassium carbonate, etc.) and the guanidine derivative are used in an amount of about 1-2 molar equivalents per mole of the compound of Formula 3, and the reaction temperature ranges from room temperature to the reflux temperature of the solvent.

The compound of Formula 5 is allowed to react with an oxidizing agent (for example, m-chloroperbenzoic acid, hydrogen peroxide, oxone, etc.) in a solvent (for example, methylenechloride, dichloroethene, methanol, ethanol, propanol, isopropanol, butanol, benzene, toluene, xylene, ethyl acetate, tetrahydrofuran, acetonitrile, N,N-dimethylformamide, dimethylsulfoxide, water, or a mixed solvent of two or more thereof) to prepare a compound of Formula 6. The oxidizing agent is used in an amount of about 1-3 molar equivalents based on the compound of Formula 5, and the reaction temperature ranges from 0° C. to the reflux temperature of the solvent.

Then, the compound of Formula 6 is allowed to react with an amine NR₃R₄ derivative in a solvent (for example, methanol, ethanol, propanol, isopropanol, butanol, benzene, toluene, xylene, ethyl acetate, tetrahydrofuran, acetonitrile, N,N-dimethylformamide, dimethylsulfoxide, water, or a mixed solvent of two or more thereof) to prepare the desired compound of Formula 1. The amine NR₃R₄ derivative is used in an amount of about 1-3 molar equivalents per mole of the compound of Formula 6, and the reaction temperature ranges from room temperature to the reflux temperature of the solvent.

Typical examples of 1,3,5-triazine-2,4,6-triamine derivatives represented by Formula 1, which are prepared according to the present invention, are shown in Table 1 below.

TABLE 1

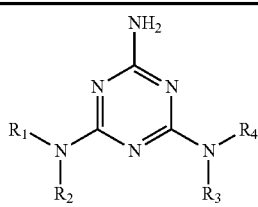

| Example | $R_1$ | $R_2$ | $R_3$ | $R_4$ |
|---|---|---|---|---|
| 1 | CH₃ | CH₃ | H | piperonyl |
| 2 | CH₃ | CH₃ | H | 3-BrPh |
| 3 | CH₃ | CH₃ | H | 4-morpholinoCH₂CH₂ |
| 4 | CH₃ | CH₃ | H | 2-pyridinylCH₂ |
| 5 | CH₃ | CH₃ | H | 2-furylCH₂ |
| 6 | H | H | H | piperonyl |
| 7 | CH₃ | CH₃ | H | piperidineCH₂CH₂ |
| 8 | CH₃ | CH₃ | H | 3-OH-4-OMePhCH₂ |
| 9 | CH₃ | CH₃ | H | CH₂CH₂CH₂pyrrolidine-2-one |
| 10 | CH₃ | CH₃ | CH₃ | CH₃ |
| 11 | CH₃ | CH₃ | H | H |
| 12 | CH₃ | CH₃ | H | 3-furylCH₂ |
| 13 | H | H | H | phenylethyl |
| 14 | CH₃ | CH₃ | H | 4-MePhCH₂ |
| 15 | CH₃ | CH₃ | H | 4-MeOPh |
| 16 | CH₃ | CH₃ | H | 3,5-(MeO)₂Ph |
| 17 | CH₃ | CH₃ | H | 3,4-Cl₂Ph |
| 18 | CH₃ | CH₃ | H | 4-BrPh |
| 19 | CH₃ | CH₃ | H | 2,5-(MeO)₂Ph |
| 20 | CH₃ | CH₃ | H | 4-ClPh |
| 21 | CH₃ | CH₃ | H | 1-naphtaleneCH₂CH₂ |
| 22 | CH₃ | CH₃ | H | 4-t-BuPh |
| 23 | CH₃ | CH₃ | H | indenyl |

TABLE 1-continued

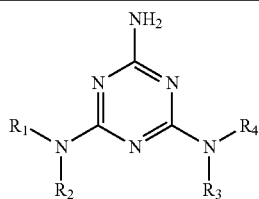

| Example | $R_1$ | $R_2$ | $R_3$ | $R_4$ |
|---|---|---|---|---|
| 24 | CH₃ | CH₃ | H | 3,5-Cl₂Ph |
| 25 | CH₃ | CH₃ | H | fluorenyl |
| 26 | CH₃ | CH₃ | H | 2-propylPh |
| 27 | CH₃ | CH₃ | H | 4-propylPh |
| 28 | CH₃ | CH₃ | H | 4-isopropylPh |
| 29 | CH₃ | CH₃ | H | hexyl |
| 30 | CH₃ | CH₃ | H | 2-FPh |
| 31 | CH₃ | CH₃ | H | 4-FPh |
| 32 | CH₃ | CH₃ | H | 3-MePh |
| 33 | CH₃ | CH₃ | H | 2-MePh |
| 34 | CH₃ | CH₃ | azepine | |
| 35 | CH₃ | CH₃ | pyrrolidine | |
| 36 | CH₃ | CH₃ | H | 2-EtPh |
| 37 | CH₃ | CH₃ | H | 4-biphenyl |
| 38 | CH₃ | CH₃ | H | 2-biphenyl |
| 39 | CH₃ | CH₃ | Ph piperazine | |
| 40 | CH₃ | CH₃ | 4-NO₂ Ph piperazine | |
| 41 | CH₃ | CH₃ | H | cyclohexyl |
| 42 | CH₃ | CH₃ | H | 4-hexylPh |
| 43 | CH₃ | CH₃ | H | 2-OHPh |

Hereinafter, the present invention will be described in more detail with reference to examples. It is to be understood, however, that these examples are given to facilitate the understanding of the construction and operation of the present invention and are not to be construed to limit the scope of the present invention.

Example 1

Preparation of N2-(benzo[d][1,3]dioxol-5-ylmethyl)-N4,N4-dimethyl-1,3,5-triazine-2,4,6-triamine (Step 1-1) Preparation of 1-(benzo[d][1,3]dioxol-5-ylmethyl)-3-cyano-2-methylisothiourea 1.6 g (10.94 mmol) of dimethyl cyanocarbonodithioimidate and 2.0 g (13.23 mmol) of piperonyl amine were dissolved in methyl alcohol, and then stirred for 30 minutes. After completion of the reaction, the produced solid was filtered, and then washed with water and methyl alcohol, thus obtaining 2.4 g (95% yield) of a desired compound of Formula 3.

¹H-NMR (300 MHz, CDCl₃) δ 2.52 (s, 3H), 4.43 (m, 2H), 5.93 (s, 2H), 6.78 (s, 3H)

(Step 1-2) Preparation of N2-(benzo[d][1,3]dioxol-5-ylmethyl)-N4,N4-dimethyl-1,3,5-triazine-2,4,6-triamine 300 mg (1.20 mmol) of 1-(benzo[d][1,3]dioxol-5-ylmethyl)-3-cyano-2-methylisothiourea was added to a solution of 328 mg (1.20 mmol) of dimethyl guanidine sulfate in 2 ml of dimethyl sulfoxide and 1 ml of 40% potassium carbonate aqueous solution. The reaction solution was refluxed at 120° C. for 5 hours, and then cooled. The product was extracted with ethyl acetate, and then the concentrated residue was purified by silica gal column chromatography (methylene chloride:methyl alcohol=95:5), thus obtaining 95 mg (53% yield) of a desired compound 1. The obtained compound 1 was dissolved in a mixed solvent of methylene chloride and methanol, and then 1.5 molar equivalents of 2M HCl (aqueous, diethyl ether and dioxane solution, etc.) was added thereto. The mixture was stirred for 1 hour, and then concentrated under reduced pressure and dried, thus obtaining a HCl salt of the desired compound of Formula 1.

mp 193.7-219.6° C.; $^1$H-NMR (300 MHz, CDCl$_3$) δ 3.06 (s, 6H), 4.45 (d, 2H), 5.03 (m, 2H), 5.52 (m, 1H), 5.91 (s, 2H), 6.73 (m, 2H), 6.81 (s, 1H); MS (ESI) 288 [M+1]$^+$

Example 2

Preparation of N2-(3-bromophenyl)-N4,N4-dimethyl-1,3,5-trizaine-2,4,6-triamine (Step 2-1) Preparation of N4,N4-dimethyl-6-methylthio-1,3,5-triazine-2,4,6-triamine 0.51 g (1.88 mmol) of dimethyl cyanocarbonodithioimidate and 0.50 g (3.42 mmol) of 1,1-dimethyl guanidine sulfate 4 were added to a mixed solution of 3.55 mL (10.26 mmol) of 40% potassium carbonate aqueous solution and 10 mL of dimethylsulfoxide. The reaction solution was stirred at 60-70° C. for 7-8 hours. The reaction solution was cooled, and then distilled water was added thereto, thus obtaining a light yellowish precipitate. The produced solid was filtered and then washed with methyl alcohol, thus obtaining 0.34 g (54% yield) of a desired compound of Formula 5 as a white solid.

mp 207-212° C.; IR (cm$^{-1}$) 3364, 3305, 3141, 2931, 1640, 1499, 1391, 1297, 990, 976, 803: $^1$H NMR (300 MHz, DMSO-d$_6$): δ6.74 (s, 2H), 3.03 (s, 6H), 2.37 (s, 3H); MS (EI) m/z 184.9 (M$^+$, 100)

(Step 2-2) Preparation of N4,N4-dimethyl-6-methylsulfinyl-1,3,5-triazine-2,4,6-triamine 0.80 g (3.24 mmol) of m-chloroperbenzoic acid was added to a solution of 0.50 g (2.70 mmol) of the compound of Formula 5 in 20 ml of methylene chloride at 0° C. in an atmosphere of argon gas. After the reaction temperature was elevated to room temperature, the reaction solution was stirred for 2 hours. After completion of the reaction, the produced white solid was filtered and washed with methylene chloride and methyl alcohol, thus obtaining a desired compound of Formula 6 as a white solid.

mp 232-235° C.; IR (cm$^{-1}$) 3364, 3305, 3141, 2931, 1640, 1499, 1391, 1297, 990, 976, 803: $^1$H NMR (300 MHz, DMSO-d$_6$): δ6.74 (s, 2H), 3.03 (s, 6H), 2.37 (s, 3H); MS (EI) m/z 184.9 (M$^+$, 100)

(Step 2-3) Preparation of N2-(3-bromophenyl)-N4, N4-dimethyl-1,3,5-triazine-2,4,6-triamine 0.12 g (0.60 mmol) of the compound of Formula 6 and 0.11 g (0.66 mmol) of 3-bromoaniline were dissolved in 10 ml of a dioxane solvent, and then refluxed at 140° C. for 8 hours. The reaction solution was cooled and concentrated, and then the solution was purified by silica gel column chromatography (methylene chloride:methyl alcohol=95:5), thus obtaining 130 mg (64% yield) of a desired compound of Formula 1. The obtained compound of Formula 1 was dissolved in a mixed solvent of methylene chloride and methanol, and then 1.5 molar equivalents of 2M HCl (aqueous, diethyl ether and dioxane solution, etc.) was added thereto. The mixture was stirred for 1 hour, and then concentrated under reduced pressure and dried, thus an HCl salt of the desired compound of Formula 1.

mp 89-92° C.; $^1$H NMR (300 MHz, CDCl$_3$): δ8.06-7.05 (m, 4H), 7.04 (s, 1H), 4.93 (br s, 2H), 3.15 (s, 6H); MS (EI) m/z 309.

All the compounds in the following Examples were synthesized according to the methods of Examples 1 and 2.

Example 3

N2,N2-dimethyl-N4-(2-morpholinoethyl)-1,3,5-triazine-2,4,6-triamine mp 138.2-141.6° C.; $^1$H NMR (DMSO-d$_6$) δ 2.47 (m, 4H), 2.53 (t, 2H), 3.10 (s, 6H), 3.47 (m, 2H), 3.71 (m, 4H), 4.67 (m, 2H), 5.27 (m, 1H); MS (ESI) m/z 268 [M+1]$^+$ Example 4

N2,N2-dimethyl-N4-(2-pyridine-3-ylmethyl)-1,3,5-triazine-2,4,6-triamine $^1$H NMR (DMSO-d$_6$) δ 3.05 (s, 6H), 4.60 (m, 2H), 4.99 (m, 2H), 5.61 (m, 1H), 7.24 (m, 1H), 7.66 (m, 1H), 8.47 (m, 1H), 8.55 (m, 1H); MS (ESI) m/z 246 [M+1]$^+$ Example 5

N2-(furan-2-ylmethyl)-N4,N4-dimethyl-1,3,5-triazine-2,4,6-triamine mp 151.6-152.0° C.; $^1$H NMR (DMSO-d$_6$) δ 3.10 (s, 6H), 4.42 (d, 2H), 4.65 (m, 2H), 4.88 (m, 1H), 6.40 (s, 1H), 7.37 (m, 2H); MS (ESI) m/z 235 [M+1]$^+$ Example 6

N2-(benzo[d][1,3]dioxol-5-ylmethyl)-1,3,5-triazine-2,4,6-triamine mp 140.8-142.9° C.; $^1$H NMR (DMSO-d$_6$) δ 4.47 (d, 2H), 4.78 (m, 3H), 5.13 (m, 1H), 5.30 (m, 1H), 5.94 (s, 2H), 6.76 (s, 2H), 6.81 (s, 1H); MS (ESI) m/z 261 [M+1]$^+$ Example 7

N2,N2-dimethyl-N4-(2-(piperidin-1-yl)ethyl)-1,3,5-triazine-2,4,6-triamine mp 116.6-117.2° C.; $^1$H NMR (DMSO-d$_6$) δ 1.44 (m, 2H), 1.58 (m, 4H), 2.42 (m, 4H), 2.50 (t, 2H), 3.09 (s, 6H), 3.47 (m, 2H)

Example 8

5-((4-amino-6-(dimethylamino)-1,3,5-triazine-2-ylamino)methyl)-2-methoxyphenol mp 141.4-142.0° C.; $^1$H NMR (DMSO-d$_6$) δ 3.09 (s, 6H), 3.86 (s, 3H), 4.48 (d 2H), 4.70 (m, 2H), 5.08 (m, 1H), 6.79 (m, 2H), 6.91 (s, 1H); MS (ESI) m/z 291 [M+1]$^+$

Example 9

1-(3-(4-amino-6-(dimethylamino)-1,3,5-triazin-2-ylamino)propyl)pyrrolidin-2-one mp 176.5-177.0° C.; $^1$H NMR (DMSO-d$_6$) δ 1.77 (m, 2H), 2.02 (m, 2H), 2.40 (m, 2H), 3.08 (s, 6H), 3.37 (m, 6H), 4.67 (m, 2H), 5.18 (m, 1H); MS (ESI) m/z 280 [M+1]$^+$

Example 10

N2,N2,N4,N4-tetramethyl-1,3,5-triazine-2,4,6-triamine mp 227.0-228.0° C.; $^1$H NMR (DMSO-d$_6$) δ 3.10 (s, 12H), 4.60 (m, 2H); MS (ESI) m/z 183 [M+1]$^+$

Example 11

N2,N2-dimethyl-1,3,5-triazine-2,4,6-triamine mp 271.8-272.8° C.; $^1$H NMR (DMSO-d$_6$) δ 3.08 (s, 6H); MS (ESI) m/z 155 [M+1]$^+$

Example: 12

N2-(furan-3-ylmethyl)-N4,N4-dimethyl-1,3,5-triazine-2,4,6-triamine mp 151.6-152.0° C.; $^1$H NMR (DMSO-d$_6$) δ 3.10 (s, 6H), 4.42 (d, 2H), 4.65 (m, 2H), 4.88 (m, 1H), 6.40 (s, 1H), 7.37 (m, 2H); MS (EST) m/z 235 [M+1]$^+$

Example 13

N2-phenethyl-1,3,5-triazine-2,4,6-triamine mp 169.9-171.8° C.; $^1$H NMR (DMSO-d$_6$) δ 2.86 (m, 2H), 3.63 (m, 2H), 4.77-4.90 (m, 5H), 7.26 (m, 5H); MS (ESI) m/z 231 [M+1]$^+$

Example 14

N2,N2-dimethyl-N4-(4-methylbenzyl)-1,3,5-triazine-2,4,6-triamine mp 139-143° C.; IR (cm$^{-1}$) 3501, 3349, 3254, 2950, 1597, 1510, 1407, 1391, 1340, 803; $^1$H NMR (DMSO-d$_6$) δ 2.32 (s, 3H), 3.07 (s, 6H), 4.54-4.52 (d, 2H), 4.72 (br s, 2H), 5.14 (br s, 1H), 7.22-7.10 (dd, 4H); MS (EI) m/z 258.0 [M]$^+$

Example 15

N2,N2-dimethyl-N4-(4-methoxyphenyl)-1,3,5-triazine-2,4,6-triamine mp 173-176° C.; $^1$H NMR (DMSO-d$_6$): δ 3.12 (s, 6H), 3.79 (s, 3H), 4.80 (br s, 2H), 6.72 (br s, 1H), 7.49-6.82 (dd, 4H)

Example 16

N2-(3,5-dimethoxyphenyl)-N4,N4-dimethyl-1,3,5-triazine-2,4,6-triamine mp 148-150° C.; $^1$H NMR (300 MHz, DMSO-d$_6$) δ 3.15 (s, 6H), 3.77 (s, 3H), 4.88 (br s, 2H), 6.15 (br s, 1H), 7.03-6.86 (m, 3H)

Example 17

N2-(3,4-dichlorophenyl)-N4,N4-dimethyl-1,3,5-triazine-2,4,6-triamine $^1$H NMR (DMSO-d$_6$) δ 3.14 (s, 6H), 4.94 (br s, 2H), 7.07 (s, 1H), 8.02-7.23 (m, 3H)

Example 18

N2-(4-bromophenyl)-N4,N4-dimethyl-1,3,5-triazine-2,4,6-triamine mp 105-108° C.; $^1$H NMR (300 MHz, DMSO-d$_6$): δ 3.13 (s, 6H), 4.95 (br s, 2H), 7.16 (br s, 1H), 7.49-7.26 (dd, 4H)

Example 19

N2-(2,5-dimethoxyphenyl)-N4,N4-dimethyl-1,3,5-triazine-2,4,6-triamine mp 213-215° C.; $^1$H NMR (300 MHz, DMSO-d$_6$) δ 3.17 (s, 6H), 3.79 (s, 3H), 3.83 (s, 3H), 4.77 (br s, 2H), 7.37 (br s, 1H), 8.28-6.45 (m, 3H)

Example 20

N2-(4-chlorophenyl)-N4,N4-dimethyl-1,3,5-triazine-2,4,6-triamine mp 164-167° C.; $^1$H NMR (300 MHz, DMSO-d$_6$) δ 3.12 (s, 6H), 4.86 (bs, 2H), 6.95 (br s, 1H), 7.56-7.23 (dd, 4H)

Example 21

N2,N2-dimethyl-N4-(1-(naphthalen-1-yl)ethyl)-1,3,5-triazine-2,4,6-triamine mp 73-76° C.; $^1$H NMR (300 MHz, DMSO-d$_6$) δ 1.66-1.63 (d 3H), 3.00 (s, 6H), 4.70 (br s, 2H), 5.20-5.28 (d, 1H), 6.05-6.0 (m, 1H), 8.21-7.40 (m, 7H)

Example 22

N2-(4-tert-butylphenyl)-N4,N4-dimethyl-1,3,5-triazine-2,4,6-triamine mp 253-263° C.; $^1$H NMR (300 MHz, DMSO-d$_6$) δ 1.26 (s, 9H), 3.15 (s, 6H), 7.37-7.52 (m, 4H); MS (ESI) m/z 286.3 [M]$^+$

Example 23

N2-(2,3-dihydro-1H-inden-5-yl)-N4,N4-dimethyl-1,3,5-triazine-2,4,6-triamine mp 245-255° C.; $^1$H NMR (300 MHz, DMSO-d$_6$) δ 1.98-2.02 (m, 2H), 2.80-2.86 (m, 4H), 3.13 (s, 6H), 7.17 (d, 1H), 7.34 (br s, 1H), 7.48 (br s, 1H); MS (ESI) m/z 270.2 [M]$^+$

Example 24

N2-(3,5-dichlorophenyl)-N4,N4-dimethyl-1,3,5-triazine-2,4,6-triamine mp 240-264° C.; $^1$H NMR (300 MHz, DMSO-d$_6$) δ 3.06 (s, 6H), 6.35 (s, 2H), 7.05 (s, 1H), 9.32 (s, 1H); MS (EST) m/z 299.1 [M]$^+$

Example 25

N2-(9H-fluoren-3-yl)-N4,N4-dimethyl-1,3,5-triazine-2,4,6-triamine mp 282-290° C.; $^1$H NMR (300 MHz, DMSO-d$_6$) δ 3.15 (s, 6H), 3.92 (s, 2H), 7.27-7.37 (m, 2H), 7.55-7.66 (m, 2H), 7.87 (m, 3H); MS (ESI) m/z 318.2 [M]$^+$

Example 26

N2,N2-dimethyl-N4-(2-propylphenyl)-1,3,5-triazine-2,4,6-triamine mp 130-145° C.; $^1$H NMR (300 MHz, DMSO-d$_6$) δ 0.87 (t, 3H), 1.51-1.54 (m, 2H), 2.54-2.57 (m, 2H), 2.98 (s, 6H), 6.20 (s, 1H), 7.02-7.05 (m, 1H), 7.11-7.16 (m, 2H), 7.45 (d, 1H), 7.95 (s, 1H); MS (ESI) m/z 272.3 [M]$^+$

Example 27

N2,N2-dimethyl-N4-(4-propylphenyl)-1,3,5-triazine-2,4,6-triamine mp 155-165° C.; $^1$H NMR (300 MHz, DMSO-d$_6$) δ 0.88 (m, 3H), 1.53-1.57 (m, 2H), 2.45-2.48 (m, 2H), 3.05 (s, 6H), 6.30 (s, 2H), 7.03 (d, 2H), 7.63 (d, 2H), 8.77 (s, 1H); MS (ESI) m/z 272.3 [M]$^+$

Example 28

N2-(4-isopropylphenyl)-N4,N4-dimethyl-1,3,5-triazine-2,4,6-triamine mp 193-201° C.; $^1$H NMR (300 MHz, DMSO-d$_6$) δ 1.17 (d, 6H), 2.54 (m, 1H), 3.11 (s, 6H), 7.70-7.72 (m, 2H), 7.89-7.90 (m, 2H), 8.77 (s, 1H); MS (ESI) m/z 283.3 [M]$^+$

Example 29

N2-hexyl-N4,N4-dimethyl-1,3,5-triazine-2,4,6-triamine mp 142-149° C.; $^1$H NMR (300 MHz, DMSO-d$_6$) δ 0.85 (t, 3H), 1.25-1.27 (m, 6H), 1.44 (br s, 2H), 3.09 (s, 6H), 3.17 (br s, 2H); MS (ESI) m/z 238.3 [M]$^+$

Example 30

N2-(2-fluorophenyl)-N4,N4-dimethyl-1,3,5-triazine-2,4,6-triamine $^1$H NMR (300 MHz, DMSO-d$_6$) δ 3.02 (s, 6H), 6.36 (s, 2H), 7.05-7.20 (m, 3H), 7.88-7.91 (m, 1H), 8.17 (s, 1H); MS (ESI) m/z 248.2 [M]$^+$

Example 31

N2-(4-fluorophenyl)-N4,N4-dimethyl-1,3,5-triazine-2,4,6-triamine mp 182-199° C.; $^1$H NMR (300 MHz, DMSO-d$_6$) δ 3.05 (s, 6H), 6.35 (s, 2H), 7.03-7.07 (m, 2H), 7.74-7.77 (m, 2H), 8.92 (s, 1H); MS (ESI) m/z 248.2 [M]$^+$

Example 32

N2,N2-dimethyl-N4-m-tolyl-1,3,5-triazine-2,4,6-triamine mp 166-168° C.; $^1$H NMR (300 MHz, DMSO-d$_6$) δ 2.09 (s, 3H), 3.07 (s, 6H), 6.32 (s, 2H), 6.72 (d, 2H), 7.56-7.65 (m, 2H), 8.76 (s, 1H); MS (ESI) m/z 244.2 [M]$^+$

Example 33

N2,N2-dimethyl-N4-o-tolyl-1,3,5-triazine-2,4,6-triamine mp 122-143° C.; $^1$H NMR (300 MHz, DMSO-d$_6$) δ 2.20 (s, 3H), 2.99 (s, 6H), 6.22 (s, 2H), 6.99-7.00 (m, 1H), 7.10-7.16 (m, 2H), 7.51 (d, 1H), 7.98 (s, 1H); MS (ESI) m/z 244.3 [M]$^+$

Example 34

6-(azepan-1-yl)-N2,N2-dimethyl-1,3,5-triazine-2,4-diamine mp 240-249° C.; $^1$H NMR (300 MHz, DMSO-d$_6$) δ 1.44-1.47 (m, 4H), 1.65 (m, 4H), 2.99 (s, 6H), 3.60 (br s, 4H), 6.08 (s, 2H); MS (EI) m/z 236.0 [M]$^+$

Example 35

N2,N2-dimethyl-6-(pyrrolidin-1-yl)-1,3,5-triazine-2,4-diamine $^1$H NMR (300 MHz, DMSO-d$_6$) δ 1.86-1.93 (m, 4H), 3.10 (s, 6H), 3.46-3.50 (m, 4H); MS (ESI) m/z 208.3 [M]$^+$

Example 36

N2-(2-ethylphenyl)-N4,N4-dimethyl-1,3,5-triazine-2,4,6-triamine $^1$H NMR (300 MHz, DMSO-d$_6$) δ 1.08 (t, 3H), 2.50 (q, 2H), 3.00 (s, 6H), 6.21 (s, 2H), 7.04-7.07 (m, 1H), 7.11-7.14 (m, 2H), 7.43 (d, 1H), 7.99 (s, 1H); MS (ESI) m/z 258.2 [M]$^+$

Example 37

N2-(biphenyl-4-yl)-N4,N4-dimethyl-1,3,5-triazine-2,4,6-triamine mp 190-201° C.; $^1$H NMR (300 MHz, DMSO-d$_6$) δ 3.16 (s, 6H), 4.85 (br s, 2H), 6.90 (s, 1H), 7.68-7.28 (m, 9H); MS (ESI) m/z 306.2 [M]$^+$

Example 38

N2-(biphenyl-2-yl)-N4,N4-dimethyl-1,3,5-triazine-2,4,6-triamine mp 196-216° C.; $^1$H NMR (300 MHz, DMSO-$d_6$) δ 2.99 (s, 6H), 6.32 (s, 2H), 7.15-7.25 (m, 2H), 7.34-7.48 (m, 7H), 8.00 (s, 1H); MS (ESI) m/z 306.2 [M]$^+$

Example 39

N2,N2-dimethyl-6-(4-phenylpiperazin-1-yl)-1,3,5-triazine-2,4-diamine mp 132-139° C.; $^1$H NMR (300 MHz, DMSO-$d_6$) δ 3.01 (s, 6H), 3.12 (t, 4H), 3.79 (t, 4H), 6.22 (s, 2H, NH2), 6.80 (t, 1H), 6.97 (d, 2H), 7.21-7.24 (m, 2H); MS (ESI) m/z 299.3 [M]$^+$

Example 40

N2,N2-dimethyl-6-(4-(4-nitrophenyl)piperazin-1-yl)-1,3,5-triazine-2,4-diamine mp 173-182° C.; $^1$H NMR (300 MHz, DMSO-$d_6$) δ 3.02 (s, 6H), 3.51 (m, 4H), 3.80 (t, 4H), 6.26 (s, 2H), 7.04 (d, 2H), 8.07 (d, 2H); MS (ESI) m/z 344.2 [M]$^+$

Example 41

N2-cyclohexyl-N4,N4-dimethyl-1,3,5-triazine-2,4,6-triamine mp 119-120° C.; $^1$H NMR (300 MHz, DMSO-$d_6$) δ 1.17-1.25 (m, 4H), 1.57-1.58 (m, 2H), 1.68-1.79 (m, 5H), 3.00 (s, 6H); MS (ESI) m/z 236.2 [M]$^+$

Example 42

N2-(4-hexylphenyl)-N4,N4-dimethyl-1,3,5-triazine-2,4,6-triamine mp 132-168° C.; $^1$H NMR (300 MHz, DMSO-$d_6$) δ 0.84-0.86 (m, 3H), 1.25-1.28 (m, 8H), 1.51-1.54 (m, 2H), 3.05 (s, 6H), 6.30 (s, 2H), 7.02 (d, 2H), 7.63 (d, 2H), 8.76 (s, 1H); MS (ESI) m/z 314.3 [M]$^+$

Example 43

2-(4-amino-6-(dimethylamino)-1,3,5-triazine-2-ylamino)phenol mp 307-312° C.; $^1$H NMR (300 MHz, DMSO-$d_6$) δ 3.05 (s, 6H), 6.56 (s, 2H), 6.74-6.77 (m, 1H), 6.81-6.88 (m, 2H), 7.74 (d, 1H), 8.04 (s, 1H); Mass (ESI) m/z 246.3 [M]$^+$ Measurement of AMPK-Related Cellular Activity Background of Experiments Metformin that is widely used in type 2 diabetic patients inhibits the formation of glucose, the synthesis of cholesterol and triglyceride in liver cells and promote the absorption of glucose from blood vessels in the muscle cells. All such processes occur through the activation of AMPK by metformin, and the function of the inventive compounds as diabetes therapeutic agents was elucidated by measuring the inhibition of gluconeogenesis, the inhibition of synthesis of cholesterol and triglyceride and the glucose absorption ability of cells, which are typical indices of AMPK activity. In the case of the ability to form cholesterol, triglyceride and glucose, the lower the numerical value, the better the effect. Numerical values for a control group become reference values. The glucose absorption ability is measured using insulin and the control group simultaneously, and values of more than 200% in consideration of deviations on the basis of cell-based experiments are determined to have glucose absorption ability.

Experimental Example 1

Measurement of Cholesterol Synthesis Ability

As a hepatic cell model, HepG2 cells were used to measure cholesterol synthesis inhibitory ability, which is the important function of AMPK. The hepatic cell model HepG2 cells were cultured in 1% serum-containing media for 24 hours, and then treated with each of the compounds for 24 hours. Then, the cells were disrupted with lysis buffer (0.1 M potassium phosphate, pH 7.4, 0.05 M NaCl, 5 mM cholic acid, 0.1% Triton X-100). To the disrupted cells, the same volume of a reaction solution (2 U/ml cholesterol oxidizing agent, 2 U/ml peroxidase, 0.2 U/ml cholesterol esterase, and 300 μM Amplex red as a fluorescent factor) was added and allowed to react at 37° C. for 30 minutes. After completion of the reaction, the cells were measured with a fluorometer at a wavelength of 560/590 nm (ex/em), thus quantifying the amount of triglyceride formed in the cells. A lower measurement value means an increased lipid production inhibitory ability. The control group showed a synthesis ability of 83.53% on average at a concentration of 2 mM. If the inventive compounds showed a synthesis ability of less than 83.53%, they were determined to be superior to the control group by comparison of the used amounts. For example, the compound of Example 25 showed cholesterol synthesis amount, which was lower than that of the control group at a concentration of 100 μM, suggesting that the effect of the compound was at least 20 times better than that of the control group.

| Compound | % control (2 mM) |
|---|---|
| Metformin | 83.53 |

| Compound | % control (250 uM) |
|---|---|
| Example 1 | 81.11 |
| Example 3 | 112.98 |
| Example 4 | 93.66 |
| Example 5 | 77.45 |
| Example 6 | 92.68 |

| Compound | % control (100 uM) |
|---|---|
| Example 2 | 23.15 |
| Example 7 | 97.4 |
| Example 8 | 59.1 |
| Example 9 | 93.5 |
| Example 10 | 98.9 |
| Example 11 | 97.7 |
| Example 12 | 92.4 |
| Example 13 | 92.3 |
| Example 14 | 87.8 |
| Example 15 | 57.10 |
| Example 16 | 66.91 |
| Example 17 | 11.30 |
| Example 18 | 66.36 |
| Example 19 | 69.15 |
| Example 20 | 56.33 |
| Example 21 | 56.57 |
| Example 22 | 53.01 |
| Example 23 | 62.98 |

| | |
|---|---|
| Example 24 | 55.84 |
| Example 25 | 76.77 |
| Example 26 | 62.89 |
| Example 27 | 63.48 |
| Example 28 | 65.88 |
| Example 29 | 63.54 |
| Example 30 | 75.72 |
| Example 31 | 67.21 |
| Example 32 | 34.22 |
| Example 33 | 65.84 |
| Example 34 | 52.60 |
| Example 35 | 69.03 |
| Example 36 | 51.01 |
| Example 37 | 66.75 |
| Example 38 | 55.10 |
| Example 39 | 55.84 |
| Example 40 | 62.24 |
| Example 41 | 70.84 |
| Example 42 | 39.02 |
| Example 43 | 41.14 |

(Effects of compounds of Examples 1, 5, 2, 8, 15, 16, 17, 18, 19, 20, 21, 22, 23, 24, 25, 26, 27, 28, 29, 30, 31, 32, 33, 34, 35, 36, 37, 38, 39, 40, 41, 42 and 43 were at least 20 times better than that of the control group).

Experimental Example 2

Measurement of Triglyceride

As a hepatic cell model, HepG2 cells were cultured in 1% serum-containing media for 24 hours, and then treated with each of the compounds for 24 hours. Then, the cells were disrupted with lysis buffer (0.1M potassium phosphate, pH 7.4, 0.05 M NaCl, 5 mM cholic acid, 0.1% Triton X-100). To the disrupted cells, the same volume of a reaction solution (0.76 U/ml glycerol kinase, 151333 U/ml peroxidase, 22.2 U/ml glycerol oxidizing agent, and 300 μM Amplex red as a fluorescent factor) was added and allowed to react at 37° C. for 30 minutes. After completion of the reaction, the cells were measured with a fluorometer at a wavelength of 560/590 nm (ex/em), thus quantifying the amount of triglyceride formed in the cells. A lower measurement value means an increased lipid production inhibitory ability. The control group showed a triglyceride synthesis ability of 70.57% on average at a concentration of 2 mM. Like the case of cholesterol synthesis ability, superiority is determined by comparison of the used amount at 70.57%

| Compound | % control (2 mM) |
|---|---|
| Metformin | 70.57 |

| Compound | % control (250 uM) |
|---|---|
| Example 1 | 103.34 |
| Example 3 | 98.02 |
| Example 4 | 99.48 |
| Example 5 | 90.23 |
| Example 6 | 108.09 |

| Compound | % control (100 uM) |
|---|---|
| Example 2 | 19.11 |
| Example 7 | 95.8 |
| Example 8 | 106.3 |
| Example 9 | 95.2 |
| Example 10 | 97.0 |
| Example 11 | 97.6 |
| Example 12 | 87.7 |

| | |
|---|---|
| Example 13 | 103.4 |
| Example 14 | 92.0 |
| Example 15 | 53.65 |
| Example 16 | 79.54 |
| Example 17 | −12.14 |
| Example 18 | 44.59 |
| Example 19 | 74.51 |
| Example 20 | 41.37 |
| Example 21 | 71.02 |
| Example 22 | 34.35 |
| Example 23 | 37.23 |
| Example 24 | 41.71 |
| Example 25 | 30.23 |
| Example 26 | 38.59 |
| Example 27 | 67.38 |
| Example 28 | 43.17 |
| Example 29 | 41.20 |
| Example 30 | 81.10 |
| Example 31 | 69.84 |
| Example 32 | 66.59 |
| Example 33 | 91.92 |
| Example 34 | 70.88 |
| Example 35 | 99.90 |
| Example 36 | 75.08 |
| Example 37 | 80.62 |
| Example 38 | 63.26 |
| Example 39 | 95.32 |
| Example 40 | 110.12 |
| Example 41 | 90.93 |
| Example 42 | 34.29 |
| Example 43 | 77.03 |

(Effects of Examples 2, 15, 17, 18, 20, 21, 22, 23, 24, 25, 26, 27, 28, 29, 31, 32, 34, 38 and 42 were at least 20 times better than the control group).

Experimental Example 3

Measurement of Gluconeogenesis

As a hepatic cell model, HepG2 cells were cultured in 10% serum-containing high glucose media, and then treated with each of the compounds for 24 hours. Then, the cells were treated with 0.5 uCi 14C-lactate and 10 mM L-lactate, and cultured for 4 hours. After cultivation, the media of the cells were removed, and the cells were washed with PBS, treated with 0.1N NaOH and left to stand at room temperature for 1 hour. Then, the cells were neutralized with 1N HCl, and the amount of glucose formed in the cells was measured with a liquid scintillation counter. The control group showed a synthesis ability of about 52.73% at a concentration of 2 mM. Like the case of cholesterol synthesis ability, if the inventive compounds showed a synthesis ability of less than 52.73%, they were determined to be superior to the control group by comparison of the used amounts. A lower measurement value means a stronger blood glucose lowering activity.

| Compound | % control (2 mM) |
|---|---|
| Metformin | 52.73 |

| Compound | % control (500 uM) |
|---|---|
| Example 1 | 104.81 |
| Example 3 | 67.57 |
| Example 4 | 92.14 |
| Example 5 | 68.54 |
| Example 6 | 82.32 |

-continued

| Compound | % control (200 uM) |
|---|---|
| Example 7 | 100.63 |
| Example 8 | 94.77 |
| Example 9 | 109.72 |
| Example 10 | 87.18 |
| Example 11 | 70.43 |
| Example 12 | 78.60 |
| Example 13 | 99.59 |

| Compound | % control (100 uM) |
|---|---|
| Example 2 | 51.89 |
| Example 14 | 75.4 |
| Example 15 | 114.18 |
| Example 16 | 87.61 |
| Example 17 | 15.16 |
| Example 18 | 66.97 |
| Example 19 | 115.57 |
| Example 20 | 84.89 |
| Example 21 | 42.15 |
| Example 22 | — |
| Example 23 | 10.73 |
| Example 24 | 49.89 |
| Example 25 | 49.51 |
| Example 26 | 24.72 |
| Example 27 | 30.90 |
| Example 28 | 45.41 |
| Example 29 | 16.31 |
| Example 30 | 85.47 |
| Example 31 | 80.71 |
| Example 32 | 66.81 |
| Example 33 | 95.59 |
| Example 34 | 39.44 |
| Example 35 | 91.39 |
| Example 36 | 42.10 |
| Example 37 | 85.68 |
| Example 38 | 13.79 |
| Example 39 | 77.43 |
| Example 40 | 39.83 |
| Example 41 | 90.56 |
| Example 42 | — |
| Example 43 | 83.50 |

(Effects of Examples 2, 17, 21, 23, 24, 25, 26, 27, 28, 34, 36, 38 and 40 were at least 20 times better than the control group).

Experimental Example 4

Measurement of Glucose Absorption

As a muscle cell model, C2C12 cells were induced to differentiate into muscle cells in 2% bovine fetal serum for 6 days. The C2C12 cells which differentiated into muscle cells were treated with each of the compounds in serum-free low glucose media, and then cultured with 1 μM of insulin for 24 hours. After cultivation, the cells were treated with 1 μCi 3H-deoxy-glucose and 10 μM deoxy-glucose at 37° C. for 15 minutes. After treatment, the media were removed, and the cells were washed twice with PBS. The washed cells were treated with 0.1 N NaOH and neutralized with 1N HCl. The amount of glucose absorbed into the cells was measured with a liquid scintillation counter. The effect of the compounds was determined by selecting a compound showing an absorption effect of at least 200%, dividing the absorption effect by the average percent of the control group, and then multiplying the divided value by 20. A higher measurement value means a stronger ability to reduce insulin resistance.

| Compound | % control (2 mM) |
|---|---|
| Metformin | 329.39 |

| Compound | % control (250 uM) |
|---|---|
| Example 1 | 133.24 |
| Example 3 | 131.90 |
| Example 4 | 143.92 |
| Example 5 | 142.38 |
| Example 6 | 113.97 |

| Compound | % control (200 uM) |
|---|---|
| Example 7 | 131.05 |
| Example 8 | 126.17 |
| Example 9 | 119.95 |
| Example 10 | 101.86 |
| Example 11 | 106.29 |
| Example 12 | 180.41 |
| Example 13 | 115.04 |

| Compound | % control (100 uM) |
|---|---|
| Example 2 | 35.23 |
| Example 14 | 113.1 |
| Example 15 | 91.06 |
| Example 16 | 63.25 |
| Example 17 | 7.29 |
| Example 18 | 91.45 |
| Example 19 | 130.71 |
| Example 20 | 132.27 |
| Example 21 | 140.06 |
| Example 22 | — |
| Example 23 | 1.91 |
| Example 24 | 136.44 |
| Example 25 | 106.66 |
| Example 26 | 170.06 |
| Example 27 | 4.05 |
| Example 28 | 173.00 |
| Example 29 | 94.48 |
| Example 30 | 132.67 |
| Example 31 | 131.08 |
| Example 32 | 118.14 |
| Example 33 | 148.04 |
| Example 34 | 202.59 |
| Example 35 | 285.09 |
| Example 36 | 100.32 |
| Example 37 | 151.21 |
| Example 38 | 92.14 |
| Example 39 | 115.19 |
| Example 40 | 244.51 |
| Example 41 | 263.44 |
| Example 42 | — |
| Example 43 | 186.21 |

(The effect of reducing insulin resistance was about 12 times better for Example 34, about 17 times better for Example 35, about 14 times better for Example 40 and about 16 times better for Example 41 than the control group).

The invention claimed is:
1. A 1,3,5-triazine-2,4,6-triamine compound or a pharmaceutically acceptable salt thereof,

[Formula 1]

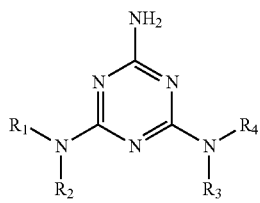

wherein the compound is selected from the group consisting of:
N2,N2-dimethyl-N4-(4-methoxyphenyl)-1,3,5-triazine-2,4,6-triamine;
N2-(3,5-dimethoxyphenyl)-N4,N4-dimethyl-1,3,5-triazine-2,4,6-triamine;
N2-(2,5-dimethoxyphenyl)-N4,N4-dimethyl-1,3,5-triazine-2,4,6-triamine;
N2,N2-dimethyl-N4-(1-(naphthalen-1-yl)ethyl)-1,3,5-triazine-2,4,6-triamine;
N2-(4-tert-butylphenyl)-N4,N4-dimethyl-1,3,5-triazine-2,4,6-triamine;
N2-(2,3-dihydro-1H-inden-5-yl)-N4,N4-dimethyl-1,3,5-triazine-2,4,6-triamine;
N2-(9H-fluoren-3-yl)-N4,N4-dimethyl-1,3,5-triazine-2,4,6-triamine;
N2,N2-dimethyl-N4-(2-propylphenyl)-1,3,5-triazine-2,4,6-triamine;
N2,N2-dimethyl-N4-(4-propylphenyl)-1,3,5-triazine-2,4,6-triamine;
N2-(4-isopropylphenyl)-N4,N4-dimethyl-1,3,5-triazine-2,4,6-triamine;
N2-hexyl-N4,N4-dimethyl-1,3,5-triazine-2,4,6-triamine;
N2,N2-dimethyl-N4-m-tolyl-1,3,5-triazine-2,4,6-triamine;
N2,N2-dimethyl-N4-o-tolyl-1,3,5-triazine-2,4,6-triamine;
6-(azepan-1-yl)-N2,N2-dimethyl-1,3,5-triazine-2,4-diamine;
N2,N2-dimethyl-6-(pyrrolidin-1-yl)-1,3,5-triazine-2,4-diamine;
N2-(2-ethylphenyl)-N4,N4-dimethyl-1,3,5-triazine-2,4,6-triamine;
N2-(biphenyl-4-yl)-N4,N4-dimethyl-1,3,5-triazine-2,4,6-triamine;
N2-(biphenyl-2-yl)-N4,N4-dimethyl-1,3,5-triazine-2,4,6-triamine;
N2,N2-dimethyl-6-(4-phenylpiperazin-1-yl)-1,3,5-triazine-2,4-diamine;
N2,N2-dimethyl-6-(4-(4-nitrophenyl)piperazin-1-yl)-1,3,5-triazine-2,4-diamine;
N2-(4-hexylphenyl)-N4,N4-dimethyl-1,3,5-triazine-2,4,6-triamine; and
2-(4-amino-6-(dimethylamino)-1,3,5-triazine-2-ylamino)phenol.

2. The 1,3,5-triazine-2,4,6-triamine compound or pharmaceutically acceptable salt of claim 1, wherein the pharmaceutically acceptable salt is a salt with formic acid, acetic acid, propionic acid, lactic acid, butyric acid, isobutyric acid, trifluoroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranilic acid, benzenesulfonic acid, p-toluenesulfonic acid or methansulfonic acid, or a salt with hydrochloric acid, bromic acid, sulfuric acid, phosphoric acid, nitric acid, carbonic acid or boric acid.

3. A method for treating a metabolic syndrome, which comprises the step of administering a pharmaceutical composition comprising a 1,3,5-triazine-2,4,6-triamine compound or pharmaceutically acceptable salt thereof,
wherein the compound is selected from the group consisting of:
N2,N2-dimethyl-N4-(4-methoxyphenyl)-1,3,5-triazine-2,4,6-triamine;
N2-(3,5-dimethoxyphenyl)-N4,N4-dimethyl-1,3,5-triazine-2,4,6-triamine;
N2-(2,5-dimethoxyphenyl)-N4,N4-dimethyl-1,3,5-triazine-2,4,6-triamine;
N2,N2-dimethyl-N4-(1-(naphthalen-1-yl)ethyl)-1,3,5-triazine-2,4,6-triamine;
N2-(4-tert-butylphenyl)-N4,N4-dimethyl-1,3,5-triazine-2,4,6-triamine;
N2-(2,3-dihydro-1H-inden-5-yl)-N4,N4-dimethyl-1,3,5-triazine-2,4,6-triamine;
N2-(9H-fluoren-3-yl)-N4,N4-dimethyl-1,3,5-triazine-2,4,6-triamine;
N2,N2-dimethyl-N4-(2-propylphenyl)-1,3,5-triazine-2,4,6-triamine;
N2,N2-dimethyl-N4-(4-propylphenyl)-1,3,5-triazine-2,4,6-triamine;
N2-(4-isopropylphenyl)-N4,N4-dimethyl-1,3,5-triazine-2,4,6-triamine;
N2-hexyl-N4,N4-dimethyl-1,3,5-triazine-2,4,6-triamine;
N2,N2-dimethyl-N4-m-tolyl-1,3,5-triazine-2,4,6-triamine;
N2,N2-dimethyl-N4-o-tolyl-1,3,5-triazine-2,4,6-triamine;
6-(azepan-1-yl)-N2,N2-dimethyl-1,3,5-triazine-2,4-diamine;
N2,N2-dimethyl-6-(pyrrolidin-1-yl)-1,3,5-triazine-2,4-diamine;
N2-(2-ethylphenyl)-N4,N4-dimethyl-1,3,5-triazine-2,4,6-triamine;
N2-(biphenyl-4-yl)-N4,N4-dimethyl-1,3,5-triazine-2,4,6-triamine;
N2-(biphenyl-2-yl)-N4,N4-dimethyl-1,3,5-triazine-2,4,6-triamine;
N2,N2-dimethyl-6-(4-phenylpiperazin-1-yl)-1,3,5-triazine-2,4-diamine;
N2,N2-dimethyl-6-(4-(4-nitrophenyl)piperazin-1-yl)-1,3,5-triazine-2,4-diamine;
N2-(4-hexylphenyl)-N4,N4-dimethyl-1,3,5-triazine-2,4,6-triamine; and
2-(4-amino-6-(dimethylamino)-1,3,5-triazine-2-ylamino)phenol, to a patient in need thereof.

4. The method of claim 3, wherein the metabolic syndrome is hyperglycemia, obesity, hyperlipidemia or hypercholesterolemia.

5. A method for treating diabetes, which comprises the step of administering a pharmaceutical composition comprising a 1,3,5-triazine-2,4,6-triamine compound or pharmaceutically acceptable salt thereof, wherein the compound is selected from the group consisting of:
N2,N2-dimethyl-N4-(4-methoxyphenyl)-1,3,5-triazine-2,4,6-triamine;
N2-(3,5-dimethoxyphenyl)-N4,N4-dimethyl-1,3,5-triazine-2,4,6-triamine;
N2-(2,5-dimethoxyphenyl)-N4,N4-dimethyl-1,3,5-triazine-2,4,6-triamine;
N2,N2-dimethyl-N4-(1-(naphthalen-1-yl)ethyl)-1,3,5-triazine-2,4,6-triamine;
N2-(4-tert-butylphenyl)-N4,N4-dimethyl-1,3,5-triazine-2,4,6-triamine;
N2-(2,3-dihydro-1H-inden-5-yl)-N4,N4-dimethyl-1,3,5-triazine-2,4,6-triamine;
N2-(9H-fluoren-3-yl)-N4,N4-dimethyl-1,3,5-triazine-2,4,6-triamine;
N2,N2-dimethyl-N4-(2-propylphenyl)-1,3,5-triazine-2,4,6-triamine;
N2,N2-dimethyl-N4-(4-propylphenyl)-1,3,5-triazine-2,4,6-triamine;
N2-(4-isopropylphenyl)-N4,N4-dimethyl-1,3,5-triazine-2,4,6-triamine;
N2-hexyl-N4,N4-dimethyl-1,3,5-triazine-2,4,6-triamine;
N2,N2-dimethyl-N4-m-tolyl-1,3,5-triazine-2,4,6-triamine;
N2,N2-dimethyl-N4-o-tolyl-1,3,5-triazine-2,4,6-triamine;
6-(azepan-1-yl)-N2,N2-dimethyl-1,3,5-triazine-2,4-diamine;
N2,N2-dimethyl-6-(pyrrolidin-1-yl)-1,3,5-triazine-2,4-diamine;
N2-(2-ethylphenyl)-N4,N4-dimethyl-1,3,5-triazine-2,4,6-triamine;
N2-(biphenyl-4-yl)-N4,N4-dimethyl-1,3,5-triazine-2,4,6-triamine;
N2-(biphenyl-2-yl)-N4,N4-dimethyl-1,3,5-triazine-2,4,6-triamine;
N2,N2-dimethyl-6-(4-phenylpiperazin-1-yl)-1,3,5-triazine-2,4-diamine;
N2,N2-dimethyl-6-(4-(4-nitrophenyl)piperazin-1-yl)-1,3,5-triazine-2,4-diamine;
N2-(4-hexylphenyl)-N4,N4-dimethyl-1,3,5-triazine-2,4,6-triamine; and
2-(4-amino-6-(dimethylamino)-1,3,5-triazine-2-ylamino)phenol, to a patient in need thereof.

* * * * *

UNITED STATES PATENT AND TRADEMARK OFFICE
CERTIFICATE OF CORRECTION

| | | |
|---|---|---|
| PATENT NO. | : 8,722,674 B2 | Page 1 of 1 |
| APPLICATION NO. | : 12/674886 | |
| DATED | : May 13, 2014 | |
| INVENTOR(S) | : Hyae Gyeong Cheon et al. | |

It is certified that error appears in the above-identified patent and that said Letters Patent is hereby corrected as shown below:

On the Title Page
Item (73), Assignee, please add KOREA RESEARCH INSTITUTE OF CHEMICAL TECHNOLOGY, DAEJEON (KR).

Signed and Sealed this
Sixteenth Day of December, 2014

Michelle K. Lee
*Deputy Director of the United States Patent and Trademark Office*